United States Patent
Neuber

(10) Patent No.: US 9,851,320 B2
(45) Date of Patent: Dec. 26, 2017

(54) HOUSING CLADDING MODULE WITH COLLISION IDENTIFICATION FOR MEDICAL DEVICES

(71) Applicant: Wolfgang Neuber, Pressath (DE)

(72) Inventor: Wolfgang Neuber, Pressath (DE)

(73) Assignee: Siemens Aktiengesellschaft, München (DE)

( * ) Notice: Subject to any disclaimer, the term of this patent is extended or adjusted under 35 U.S.C. 154(b) by 660 days.

(21) Appl. No.: 14/051,009

(22) Filed: Oct. 10, 2013

(65) Prior Publication Data

US 2014/0111227 A1   Apr. 24, 2014

(30) Foreign Application Priority Data

Oct. 18, 2012 (DE) .................... 10 2012 219 024

(51) Int. Cl.
*G01R 27/08* (2006.01)
*G01N 27/04* (2006.01)
(Continued)

(52) U.S. Cl.
CPC ........... *G01N 27/041* (2013.01); *A61B 6/102* (2013.01); *G01N 17/00* (2013.01); *G01N 17/006* (2013.01);
(Continued)

(58) Field of Classification Search
CPC ...... A61B 6/102; G01N 27/041; G01N 27/07; G01N 27/228; G01N 2035/1025; G01N 27/045; G01N 17/00; G01N 17/006; G01N 17/02; G01N 27/02; G01N 27/04; G01R 27/22; G01R 31/00; G01R 27/00; G01L 1/10; G01L 1/20; G01L 1/22
(Continued)

(56) References Cited

U.S. PATENT DOCUMENTS 4,733,408 A * 3/1988 Beikuefner et al. .......... 378/117
5,570,770 A   11/1996 Baaten et al.
(Continued)

FOREIGN PATENT DOCUMENTS

CN   101627320 A   1/2010
CN   101947360 A   1/2011
(Continued)

OTHER PUBLICATIONS

German Office Action dated Oct. 17, 2013 for corresponding German Patent Application No. DE 10 2012 219 024.4 with English translation.
(Continued)

*Primary Examiner* — Giovanni Astacio-Oquendo
*Assistant Examiner* — Raul Rios Russo
(74) *Attorney, Agent, or Firm* — Lempia Summerfield Katz LLC

(57) ABSTRACT

A housing cladding module for a medical device is provided for collision identification. The module includes resistor elements, which are arranged in and/or on the surface and which are designed such that the resistor elements change their electrical resistance on expansion. The resistor elements are arranged in such a way that the resistor elements are expanded in the event of a collision with an object. The collision is identified easily, and the effective collision force may be ascertained.

19 Claims, 1 Drawing Sheet

(51) Int. Cl.
  *G01N 17/00* (2006.01)
  *G01N 17/02* (2006.01)
  *A61B 6/10* (2006.01)
  *G01L 1/10* (2006.01)
  *G01L 1/22* (2006.01)
  *G01L 1/20* (2006.01)

(52) U.S. Cl.
  CPC ............... *G01N 17/02* (2013.01); *G01L 1/10* (2013.01); *G01L 1/20* (2013.01); *G01L 1/22* (2013.01)

(58) Field of Classification Search
  USPC ......... 324/76, 439, 459, 549, 600, 649, 691, 324/693, 697; 600/300, 309, 322–325, 600/332, 337, 339–341
  See application file for complete search history.

(56) References Cited

U.S. PATENT DOCUMENTS

| | | | |
|---|---|---|---|
| 5,862,803 A * | 1/1999 | Besson et al. | 600/508 |
| 5,928,149 A | 7/1999 | Habraken | |
| 6,359,458 B1 * | 3/2002 | Yoshii | G01R 31/2829 324/762.01 |
| 2003/0128121 A1 * | 7/2003 | Nee | A61N 1/37282 340/573.1 |
| 2003/0156036 A1 * | 8/2003 | Stuetzler | B60R 21/0136 340/665 |
| 2007/0290491 A1 * | 12/2007 | Hoffmann | B60R 21/2171 280/743.1 |
| 2008/0304626 A1 | 12/2008 | Camus | |
| 2010/0061509 A1 | 3/2010 | D'Ambrosio et al. | |
| 2010/0136588 A1 * | 6/2010 | Colgin | C12Q 1/6883 435/7.92 |
| 2010/0269960 A1 * | 10/2010 | Hertz | C21D 7/06 148/558 |
| 2011/0006230 A1 | 1/2011 | Fadler | |
| 2011/0090926 A1 * | 4/2011 | Sekiguchi | B82Y 20/00 372/4 |
| 2011/0257504 A1 * | 10/2011 | Hendricks et al. | 600/395 |
| 2011/0309944 A1 | 12/2011 | Lakshminarayanan | |
| 2012/0013433 A1 * | 1/2012 | Rauh | H05B 3/34 338/296 |
| 2012/0034833 A1 * | 2/2012 | Schaube | A63C 11/227 442/172 |
| 2012/0109541 A1 * | 5/2012 | De Boissieu | G01B 5/28 702/41 |
| 2012/0145700 A1 * | 6/2012 | Tsai | H05B 3/145 219/549 |
| 2012/0192619 A1 * | 8/2012 | Muziol | G01F 1/684 73/23.31 |
| 2013/0019374 A1 * | 1/2013 | Schwartz | A61F 5/00 2/69 |
| 2013/0163728 A1 * | 6/2013 | Silberklang | A61B 6/037 378/177 |
| 2014/0225867 A1 * | 8/2014 | Schimanski | G06F 3/044 345/174 |

FOREIGN PATENT DOCUMENTS

| | | |
|---|---|---|
| CN | DE102010010873 A1 | 5/2011 |
| CN | 202086490 U | 12/2011 |
| CN | 202136349 U | 2/2012 |
| EP | 0 462 295 A1 | 12/1991 |
| WO | WO 97/19638 A1 | 6/1997 |

OTHER PUBLICATIONS

Chinese Office Action for Chinese Application No. 20130481600X, dated Jul. 16, 2015, with English Translation.

* cited by examiner

HOUSING CLADDING MODULE WITH COLLISION IDENTIFICATION FOR MEDICAL DEVICES

This application claims the benefit of DE 102012219024.4, filed on Oct. 18, 2012, which is hereby incorporated by reference in its entirety.

FIELD

The present embodiments relate to a housing cladding module, an arrangement comprising a housing cladding module and an associated method with collision identification for a medical device, for example, for an X-ray device.

BACKGROUND

A medical device of this type is known, for example, from the patent specification U.S. Pat. No. 5,570,770.

Medical devices for medical diagnosis or therapy generally have an X-ray source and an X-ray detector, in each case in a housing. These two components are arranged at a distance from one another, wherein a patient to be examined or treated is positioned between the X-ray source and the X-ray detector. The X-ray source and the X-ray detector are positioned relative to the patient's body in such a way that an image of the desired cross section of the body interior may be captured. The alignment and positioning of the medical device may usually be performed with the aid of a motor drive.

Such devices are often equipped with a C-arm (i.e., an arched holder which may be rotated about a plurality of planes with the aid of a rail system). During use of the medical device, it is important that a moving part, for example the X-ray detector, comes close to the object to be examined in order to achieve the desired image quality. The X-ray detector has a comparatively large front face for receiving the X-rays and any desired point on this front face or over its circumference could come into contact with the patient to be examined. Such a collision may take place in any movement direction of the X-ray detector. This is undesirable and therefore a device of this type is equipped with a detection apparatus for identifying the collision with an object.

If contact between the moving part of the device and the object is identified, the movement of said device may be stopped in order to thus minimize the severity of the consequences of a collision. The cited patent specification of U.S. Pat. No. 5,570,770 describes a medical X-ray device that is equipped with an electrical detection apparatus for identifying collisions. Sensors in the device are designed to measure the current consumed by the drive motor or the power consumed thereby. These variables give an indication of the instantaneous force exerted on the moving part. This instantaneous value may be compared with an expected value for this force. If the difference between the instantaneous value and the expected value exceeds a predetermined threshold value, it is assumed that the movement of the moving part is impeded by an object and therefore a collision is taking place. Accordingly, an alarm signal is generated, and the movement is stopped.

Also known are housing claddings of moveable medical devices or parts of claddings in which a collision with an object acts on an electrical switch or on electrically switchable contacts. Such housing claddings are mounted in a sprung manner, for example, wherein a shift in the position of said housing claddings as a result of a collision is identified. Furthermore, there are solutions with elastic materials which actuate the electrical switch in the event of a predeterminable flexibility. The switching signals thus obtained are used to switch off a movement of the medical device.

SUMMARY AND DESCRIPTION

The scope of the present invention is defined solely by the appended claims and is not affected to any degree by the statements within this summary. The present embodiments may obviate one or more of the drawbacks or limitations in the related art. For example, an apparatus, an arrangement comprising the apparatus and an associated method that can detect a collision of a medical device with an object are provided.

A housing cladding or part of the housing cladding is used to detect a collision with an object by virtue of a change in the electrical resistance of a resistor element. The resistor elements may be carbon fibers, for example. As a result of an expansion of the resistor elements, the electrical resistance changes. Depending on the accuracy and resolution of the detection, it is also possible to draw conclusions on the size of the deformation and thus on the force of the collision.

A housing cladding module of a medical device is provided for collision identification. Resistor elements are arranged in the module and/or on the surface of the module. The resistor elements change their electrical resistance on expansion and are arranged in such a way that they are expanded on collision with an object. A collision is identified easily and safely and the effective collision force may be detected.

In one embodiment, the resistor elements may be fibrous.

In a further embodiment, the fibrous resistor elements may be formed from carbon fibers. As a result, a simple and inexpensive embodiment is possible.

In a further embodiment, the resistor elements may be electrically insulated from one another. As a result, the location of the collision may be determined.

Furthermore, the resistor elements may form a matrix. It is advantageous that, as a result, a large area may be provided with such resistor elements.

In a further embodiment, the housing cladding module may be formed from a soft, deformable material.

An arrangement includes a housing cladding module and a resistance measurement unit, which measures changes in resistance of resistor elements.

A method for detecting a collision of an object with a housing cladding module of a medical installation is provided. A change in electrical resistance of resistor elements arranged in the housing cladding module and/or on the surface of the housing cladding module is measured.

In one embodiment of the method, the electrical resistance of the resistor elements may be changed by expansion of the resistor elements.

In a further embodiment, at least one of the resistor elements may be expanded in the event of a collision with the object.

In addition, the resistor elements may be formed by carbon fibers arranged so as to be electrically insulated from one another.

DETAIL DESCRIPTION

Figure 1:
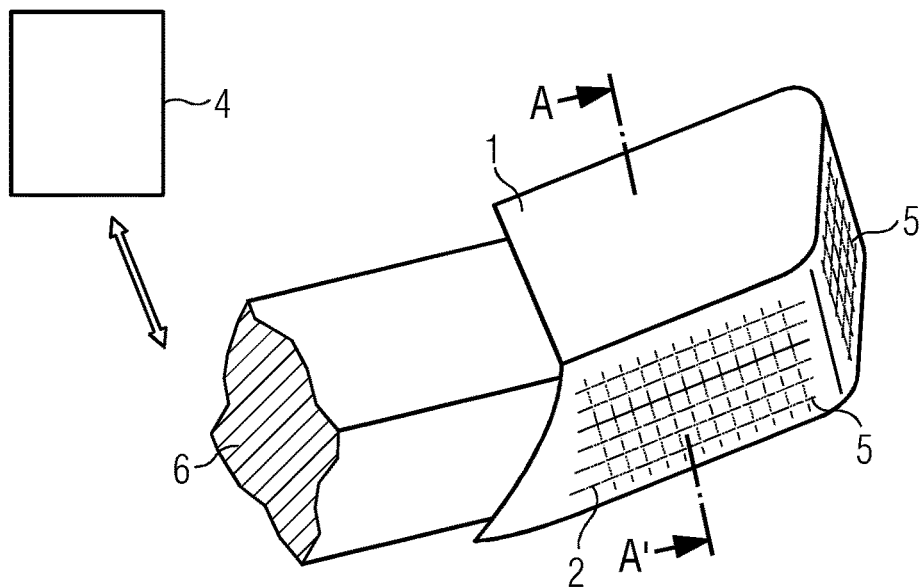
FIG. 1 shows part of one embodiment of a medical device in a perspective view.

FIG. 1 shows part of a medical device 6, whose end is provided with a housing cladding 1. The housing cladding 1 provides protection from collisions for people and the device. Carbon fibers 2 in the form of a matrix 5 are arranged in the surface of the cladding 1. Two layers of carbon fibers 2 are electrically insulated from one another. The housing cladding 1 is formed of a soft polymer, so is easily deformable. The electrical resistance of the fibers 2 is measured with the aid of a resistance measurement unit 4.

If the fibers 2 are expanded, the electrical resistance increases. The increase is detected by the resistance measurement unit 4. An expansion of the fibers 2 takes place whenever the housing cladding 1 is deformed, for example, in the event of a collision with an object. The object may be a person or an article.

The greatest change in resistance takes place on expansion in the fiber direction. Therefore, it is important to arrange the carbon fibers on the cladding part according to the shape of the cladding part and according to the most likely collision direction. "Carbon fiber threads" which do not cross over one another in their structure are to be used. Carbon fiber mats, such as are used in carbon fiber components, are not suitable for this application.

Furthermore, the design of the cladding 1 has the advantage of flexibility owing to elastic basic bodies forming the cladding. Therefore, a collision does not take place suddenly, but builds up with the resistance of the compression of the elastic basic body. Damage to obstructions or even injury to people which will be caused by the collision is therefore prevented or at least minimized.

Figure 2:
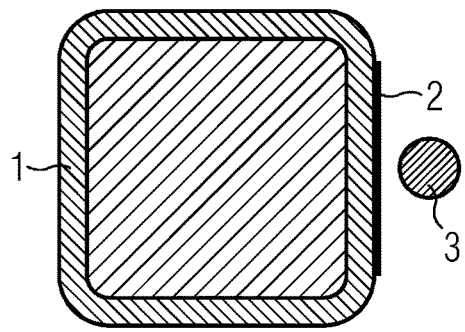
FIG. 2 shows a sectional view of an example housing cladding without collision.
Figure 3:
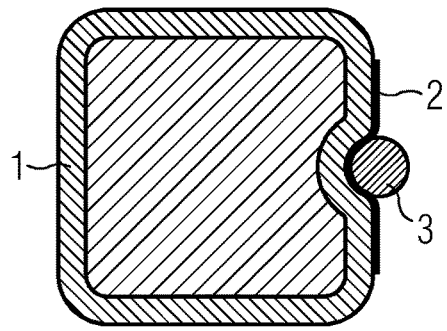
FIG. 3 shows a sectional view of another example housing cladding with collision with an object.

The reference symbols A and A' denote a section plane, of which a sectional view is shown in FIGS. 2 and 3.

FIG. 2 shows the sectional view of the housing cladding 1 along the section plane A-A' in FIG. 1. Only one carbon fiber 2 of the matrix is visible in the sectional view. An object 3 is arranged spaced apart from the cladding 1.

FIG. 3 shows the sectional view shown in FIG. 2 with the object 3 in a collided position. The housing cladding 1 is pressed in by the object 3 owing to the softness of said housing cladding. As a result of the collision, the embedded carbon fibers 2 are expanded. The electrical resistance of the carbon fibers 2 increases, which is detectable. As a result, a collision with an object may be identified and counteractive measures may be introduced. For example, a signal for stopping a movement is generated. Owing to the elasticity of the carbon fibers 2 and the softness of the housing cladding 1, the process of expansion is reversible.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A housing cladding module for collision identification of a medical device, the housing cladding module comprising:
   a housing cladding having a soft, deformable material, wherein the housing cladding is configured to be positioned on a surface of the medical device; and
   resistor elements arranged on a on an external surface of the housing cladding,
      wherein the resistor elements are configured to expand when an object collides with the housing cladding, and
      wherein the resistor elements are configured to change an electrical resistance on expansion.

2. The housing cladding module as claimed in claim 1, wherein the resistor elements are fibrous.

3. The housing cladding module as claimed in claim 2, wherein the fibrous resistor elements comprise carbon fibers.

4. The housing cladding module as claimed in claim 1, wherein the resistor elements are electrically insulated from one another.

5. The housing cladding module as claimed in claim 1, wherein the resistor elements comprise a matrix or a plurality of matrices arranged one above the other.

6. The housing cladding module as claimed in claim 3, wherein the carbon fiber resistor elements are electrically insulated from one another such that carbon fiber threads of the carbon fiber resistor elements do not cross over one another.

7. The housing cladding module as claimed in claim 3, wherein the resistor elements comprise a matrix or a plurality of matrices arranged one above the other.

8. The housing cladding module as claimed in claim 6, wherein the resistor elements comprise a matrix or a plurality of matrices arranged one above the other.

9. The housing cladding module as claimed in claim 1, wherein the resistor elements comprise carbon fibers, and
   wherein the carbon fibers are arranged on the external surface of the housing cladding according to an anticipated collision direction.

10. The housing cladding module as claimed in claim 9, wherein the carbon fiber resistor elements are electrically insulated from one another such that carbon fiber threads of the carbon fiber resistor elements do not cross over one another.

11. An arrangement comprising:
    a housing cladding module having:
       a housing cladding comprising a soft, deformable material, wherein the housing cladding is configured to be positioned on a surface of a medical device; and
       resistor elements arranged on an external surface of the housing cladding, wherein the resistor elements are configured to expand when an object collides with the housing cladding, and wherein the resistor elements are configured to change an electrical resistance on expansion; and
    a resistance measurement unit operable to measure changes in resistance of the resistor elements.

12. The arrangement as claimed in claim 11, wherein the resistor elements are fibrous.

13. The arrangement as claimed in claim 12, wherein the fibrous resistor elements comprise carbon fibers.

14. The arrangement as claimed in claim 11, wherein the resistor elements are electrically insulated from one another.

15. The arrangement as claimed in claim 11, wherein the resistor elements comprise carbon fibers, and
  wherein the carbon fibers are arranged on the external surface of the housing cladding according to an anticipated collision direction.

16. The arrangement as claimed in claim 15, wherein the carbon fiber resistor elements are electrically insulated from one another such that carbon fiber threads of the carbon fiber resistor elements do not cross over one another.

17. The arrangement as claimed in claim 13, wherein the carbon fiber resistor elements are electrically insulated from one another such that carbon fiber threads of the carbon fiber resistor elements do not cross over one another.

18. A method for detecting a collision of an object with a housing cladding module of a medical device, the method comprising:
  providing a housing cladding module comprising a housing cladding having a soft, deformable material;
  positioning the housing cladding on a surface of the medical device;
  arranging resistor elements on an external surface of the housing cladding, wherein the resistor elements are configured to expand when an object collides with the housing cladding, and wherein the resistor elements are configured to change an electrical resistance on expansion; and
  measuring a change in electrical resistance of the resistor elements when the resistor elements expand upon collision of the object with the housing cladding.

19. The method as claimed in claim 18, further comprising electrically insulating the resistor elements from one another, the resistor elements comprising carbon fibers.

\* \* \* \* \*